(12) United States Patent
Kopp, III et al.

(10) Patent No.: US 6,246,743 B1
(45) Date of Patent: Jun. 12, 2001

(54) METHODS AND APPARATUS FOR TROUBLESHOOTING SCALEABLE MULTISLICE IMAGING SYSTEM

(75) Inventors: Rudolph T. Kopp, III, Hartland; Hui David He, Waukesha; George E. Seidenschnur, Waukesha; Paul C. Schanen, Waukesha, all of WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/140,290

(22) Filed: Aug. 25, 1998

(51) Int. Cl.[7] .................................................. G01N 23/00
(52) U.S. Cl. ............................................. 378/19; 378/207
(58) Field of Search ........................................ 378/19, 207

(56) References Cited

U.S. PATENT DOCUMENTS 4,965,726 * 10/1990 Heuscher et al. ...................... 378/19
5,473,663 * 12/1995 Hsieh ..................................... 378/19

* cited by examiner

Primary Examiner—Craig E. Church
(74) Attorney, Agent, or Firm—Armstrong Teasdale LLP; Christian G. Cabow (57) ABSTRACT

The present invention, in one form, is an imaging system which, in one embodiment, alters the configuration of a detector array and a data acquisition system to determine degraded component performance and generate fault isolation information. More specifically, by altering the configuration to include different combinations of detector array cells, interconnections, and one or more data acquisition channels, fault isolation information is generated.

18 Claims, 8 Drawing Sheets

METHODS AND APPARATUS FOR TROUBLESHOOTING SCALEABLE MULTISLICE IMAGING SYSTEM

BACKGROUND OF THE INVENTION

This invention relates generally to computed tomography (CT) imaging and more particularly, to troubleshooting of an imaging system.

In at least one known CT system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector.

In an axial scan, the projection data is processed to construct an image that corresponds to a two dimensional slice taken through the object. One method for reconstructing an image from a set of projection data is referred to in the art as the filtered back projection technique. This process converts that attenuation measurements from a scan into integers called "CT numbers" or "Hounsfield units", which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a one fan beam helical scan. The helix mapped out by the fan beam yields projection data from which images in each prescribed slice may be reconstructed.

At least one known CT imaging system utilizes a detector array and a data acquisition system (DAS) for collecting image data. The detector array includes detector cells or channels that each produce an analog intensity signal which is representative of the x-ray energy impinged upon the cell. The analog signals are then supplied to the DAS for conversion to digital signals. The digital signals are then used to produce image data. Image artifacts, with the potential for patient mis-diagnosis, can be produced by the degradation or failure of individual detector cells, the DAS, and detector to DAS interconnections. Detector cell degradation as measured by gain non-linearity typically produces ring or band annoyance artifacts. In addition, failure of cells at the center of the detector results in a spot on the image, which could be interpreted as a tumor or lesion. Similarly, degradation and failure of the interconnections and DAS impact the image quality. As a result of the complexity of the imaging system troubleshooting of components may be time consuming and difficult.

Accordingly, it is desirable to provide an imaging system which detects component failure and provides fault isolation information. It would also be desirable to provide such a system without increasing the cost and complexity of the system.

BRIEF SUMMARY OF THE INVENTION

These and other objects may be attained in an imaging system which, in one embodiment, alters the configuration of a detector array and a data acquisition system to determine degraded component performance and generate fault isolation information. The imaging system includes a multislice detector array having a plurality of detector cells, an x-ray source for radiating an x-ray beam toward the detector array, a data acquisition system (DAS), and a computer.

By altering the configuration of the detector array and channel selection within the DAS, degraded components may be isolated for replacement. More specifically, detector intensity data is generated and converted by the DAS for a reference scan. If the scan data does not conform to reference data, the configuration of the detector array and DAS are altered and additional reference scans are performed to provide fault isolation information. More specifically, by altering the configuration of the detector array to include different combinations of cells, different detector intensity data are generated to identify degraded detector performance. In addition, the DAS configuration is altered so that the detector intensity data is converted by one or any number of DAS channels. By comparing the results of the different combinations, degraded interconnection and DAS performance is identified and fault isolation information is generated.

By utilizing the multislice detector array and the DAS, specific degraded components are identified. In addition, the described system reduces the time required to isolate a failure and produces repeatable results without increasing the cost and complexity of the system.

DETAILED DESCRIPTION OF THE INVENTION

Figure 1:
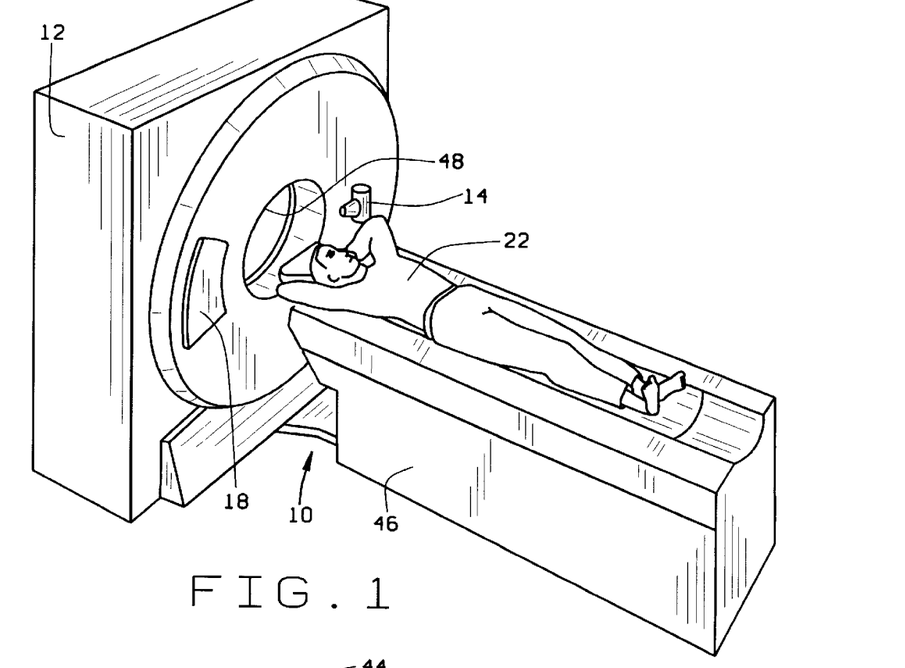
FIG. 1 is a pictorial view of a CT imaging system.
Figure 2:
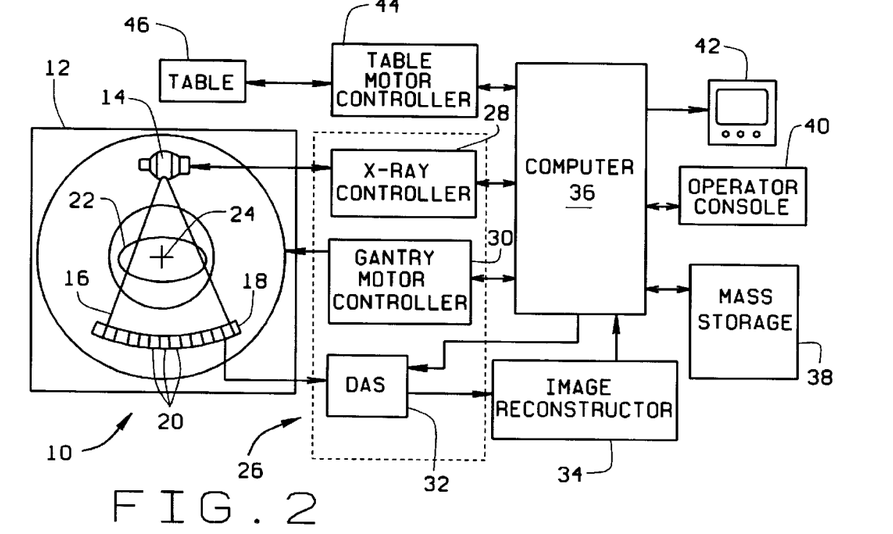
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements, or cells 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A scaleable data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives and supplies signals via a user interface, or graphical user interface (GUI). Specifically, computer receives commands and scanning parameters from an operator via console 40 that has a keyboard and a mouse (not shown). An associated cathode ray tube display 42 allows the operator to observe the reconstructed image and other data from computer 36. The operator supplied commands and parameters are used by computer 36 to provide control signals and information to x-ray controller 28, gantry motor controller 30, DAS 32, and table motor controller 44.

Figures 3, 4:
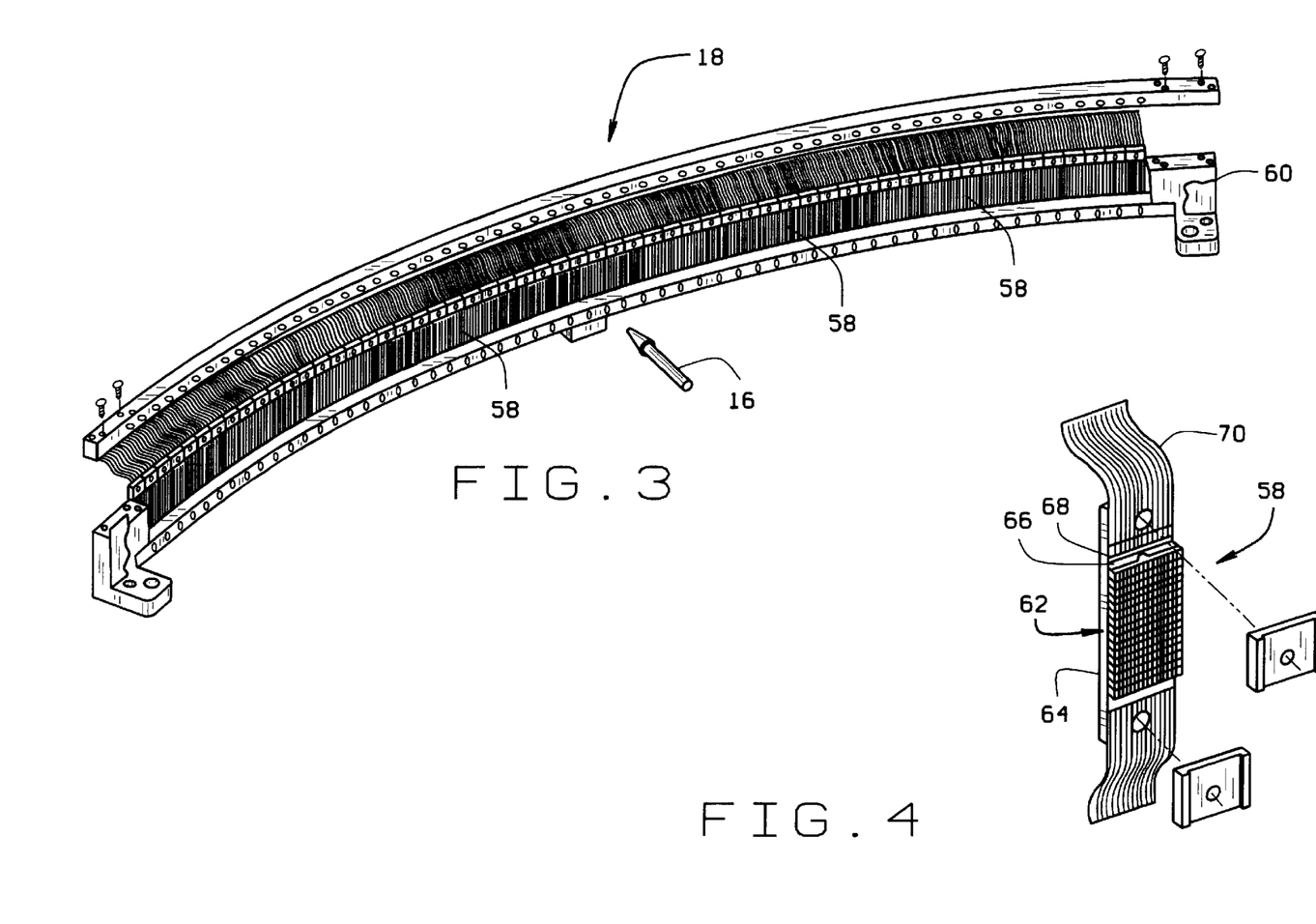
FIG. 3 is a perspective view of a CT system detector array.
FIG. 4 is a perspective view of a detector module.

As shown in FIGS. 3 and 4, detector array 18 includes a plurality of detector modules 58. Each detector module 58 is secured to a detector housing 60. Each module 58 includes a multidimensional scintillator array 62 and a high density semiconductor array (not visible). A post patient collimator (not shown) is positioned over and adjacent scintillator array 62 to collimate x-ray beams before such beams impinge upon scintillator array 62. Scintillator array 62 includes a plurality of scintillation elements arranged in an array, and the semiconductor array includes a plurality of photodiodes (not visible) arranged in an identical array. The photodiodes are deposited, or formed on a substrate 64, and scintillator array 62 is positioned over and secured to substrate 64.

Detector module 58 also includes a switch apparatus 66 electrically coupled to a decoder 68. Switch apparatus 66 is a multidimensional semiconductor switch array of similar size as the photodiode array. In one embodiment, switch apparatus 66 includes an array of field effect transistors (not shown) with each field effect transistor (FET) having an input, an output, and a control line (not shown). Switch apparatus 66 is coupled between the photodiode array and DAS 32. Particularly, each switch apparatus FET input is electrically connected to a photodiode array output and each switch apparatus FET output is electrically connected to DAS 32, for example, using flexible electrical cable 70.

Decoder 68 controls the operation of switch apparatus 66 to enable, disable, or combine the outputs of the photodiode array in accordance with a desired number of slices and slice resolutions for each slice. Decoder 68, in one embodiment, is a decoder chip or a FET controller as known in the art. Decoder 68 includes a plurality of output and control lines coupled to switch apparatus 66 and computer 36. Particularly, the decoder outputs are electrically connected to the switch apparatus control lines to enable switch apparatus 66 to transmit the proper data from the switch apparatus inputs to the switch apparatus outputs. The decoder control lines are electrically connected to the switch apparatus control lines and determine which of the decoder outputs will be enabled. Utilizing decoder 68, specific FETs within switch apparatus 66 are enabled, disable, or combined so that specific outputs of the photodiode array are electrically connected to CT system DAS 32. In one embodiment defined as a system diagnostic mode, decoder 68 enables switch apparatus 66 so that all rows of the photodiode array are electrically connected to DAS 32, resulting in 16 separate slices of data being sent to DAS 32. Of course, many other slice combinations are possible.

In one specific embodiment, detector 18 includes fifty-seven detector modules 58. The semiconductor array and scintillator array 62 each have an array size of 16×16. As a result, detector 18 has 16 rows and 912 columns (16×57 modules), which enables 16 simultaneous slices of data to be collected with each rotation of gantry 12. Of course, the present invention is not limited to any specific array size, and it is contemplated that the array can be larger or smaller depending upon the specific operator needs. Also, detector 18 may be operated in many different slice thickness and number modes, e.g., one, two, and four slice modes. For example, the FETs can be configured in the four slice mode, so that data is collected for four slices from one or more rows of the photodiode array. Depending upon the specific configuration of the FETs as defined by decoder control lines, various combinations of outputs of the photodiode array can be enabled, disabled, or combined so that the slice thickness may, for example, be 1.25 mm, 2.5 mm, 3.75 mm, or 5 mm. Additional examples include a single slice mode including one slice with slices ranging from 1.25 mm thick to 20 mm thick, and a two slice mode including two slices with slices ranging from 1.25 mm thick to 10 mm thick. Additional modes beyond those described are possible.

Figure 5A:
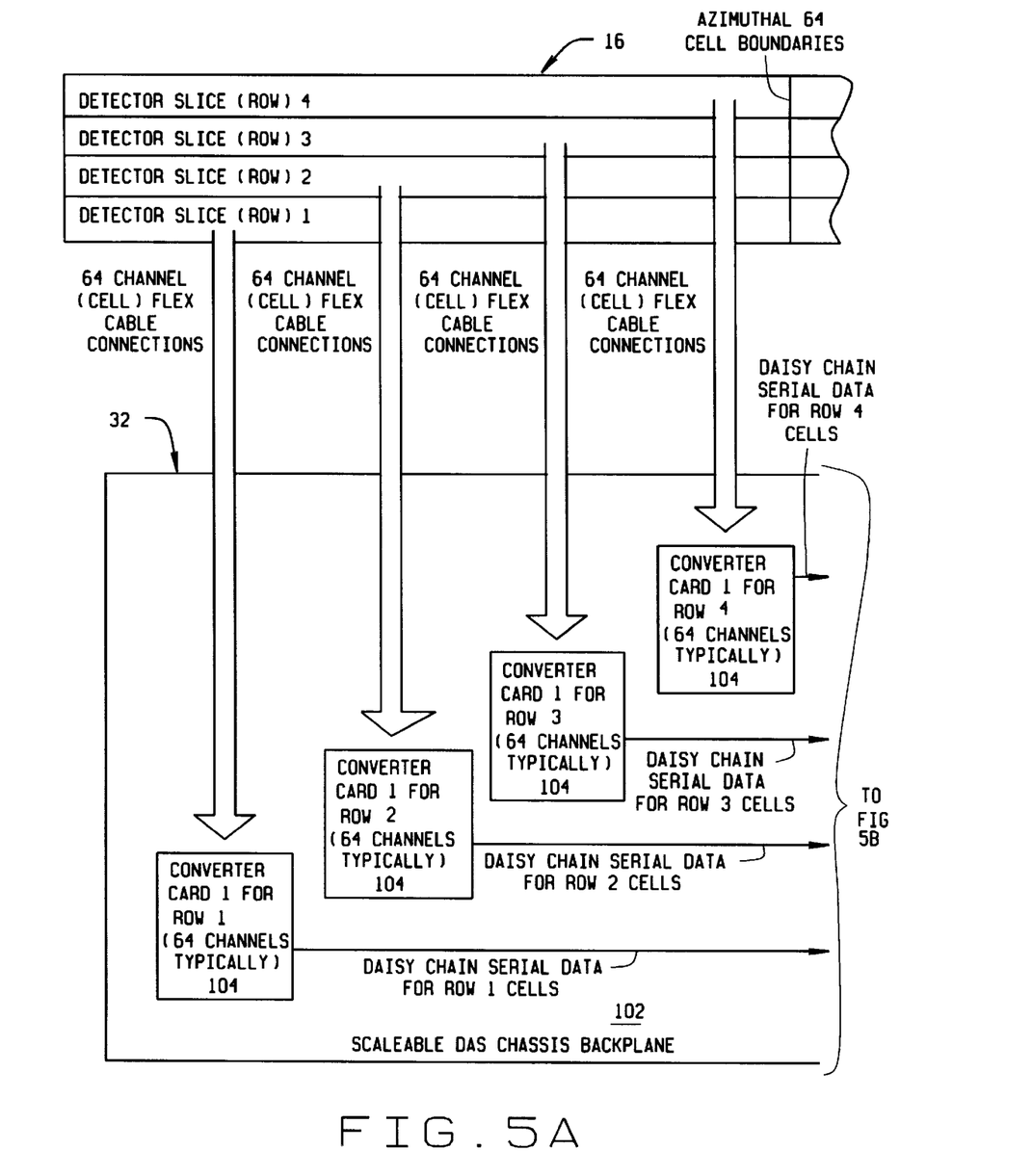
FIG. 5 is a block diagram of a scaleable data acquisition system of the CT imaging system shown in FIG. 1.
Figure 5B:
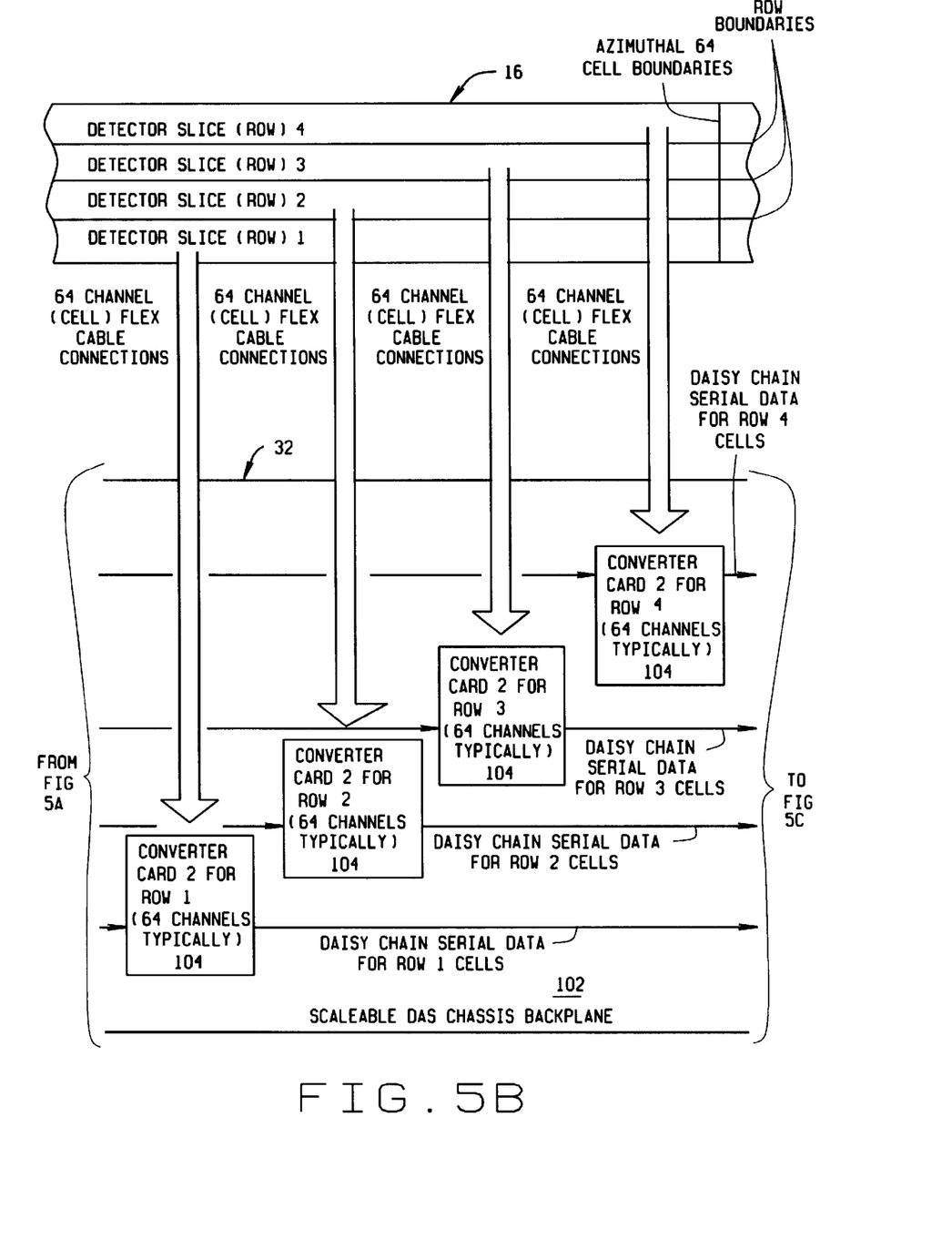
Figure 5C:
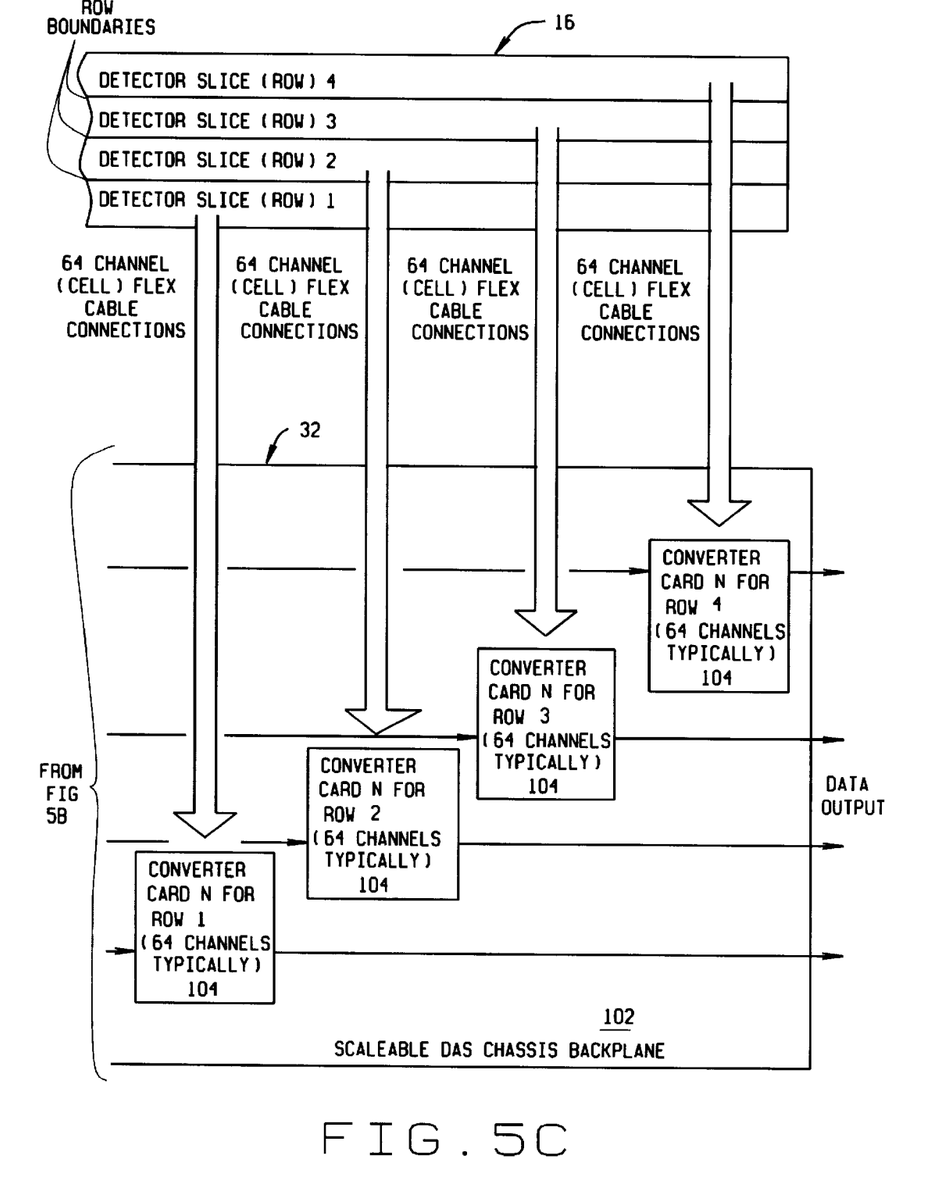

FIG. 5 is a block diagram of scalable data acquisition system (SDAS or DAS) 32 which is easily reconfigured to be used with either single slice or multi-slice CT detector systems. SDAS 32 can be reconfigured by adding or removing printed circuit boards to accommodate the number of slices provided by x-ray detector 18. SDAS 32 is configured to convert the low level electrical current signal, or intensity signals, from x-ray detector 18 to digital values for image reconstruction, display and archive. Single slice third generation, fan-beam CT systems have traditionally contained 300 to 1000 detector cells in the Azimuthal direction. SDAS 32 correspondingly is required to provide an anti-alias filter (not shown) for each cell prior to Analog to Digital Conversion (ADC). DAS cells are traditionally referred to as channels. Detector cells can be ganged or paralleled to one DAS channel. The digital output from DAS 32 is usually transmitted either in a serial or semi-serial fashion, as described below in more detail, to reduce the amount of interconnecting hardware. Analog current signals from detector 18 are supplied to input channels (not shown) of SDAS 32 via shielded ribbon or flex cables (not shown). The cables are connected to SDAS 32 at a DAS backplane 102. DAS Converter boards 104 are also plugged into DAS backplane 102. This interconnection provides several advantages. First, backplane 102 enables ganging the detector cells on the outside edges of the fan beam. Second, backplane 102 allows a redistribution of the detector cells to appropriate converter boards 104. Signals from more than one slice are contained in the same flex cable. Each converter board 104 only serves one slice since the reconfiguration of DAS 32 from one multi-slice configuration to another or to the single slice configuration requires only the removal or addition of converter boards 104. Third, backplane 102 enables a blending or weaving of DAS channels and detector cells near the end channels of a converter board 104.

Another aspect of the SDAS 32 is converter boards 104 which combine the anti-alias filter and ADC on the same board rather on separate boards. Having the filter and ADC on the same board 104 enables the modularity required for scalable DAS 42. The integrated filter-ADC function on the same board also limits the possibility of electromagnetic and conducted interference because of short electrical lead lengths.

Figure 6A:
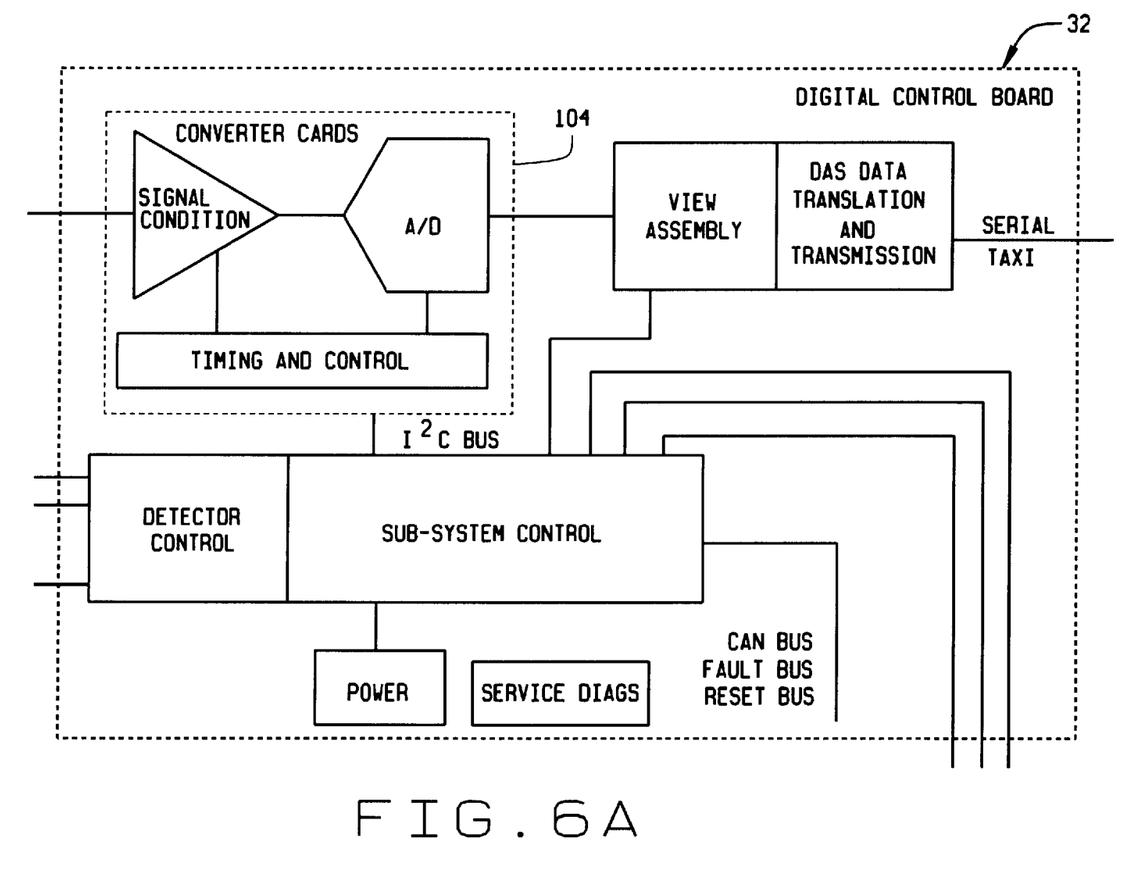
FIG. 6 is a functional block diagram of the scaleable data acquisition system shown in FIG. 5.
Figure 6B:
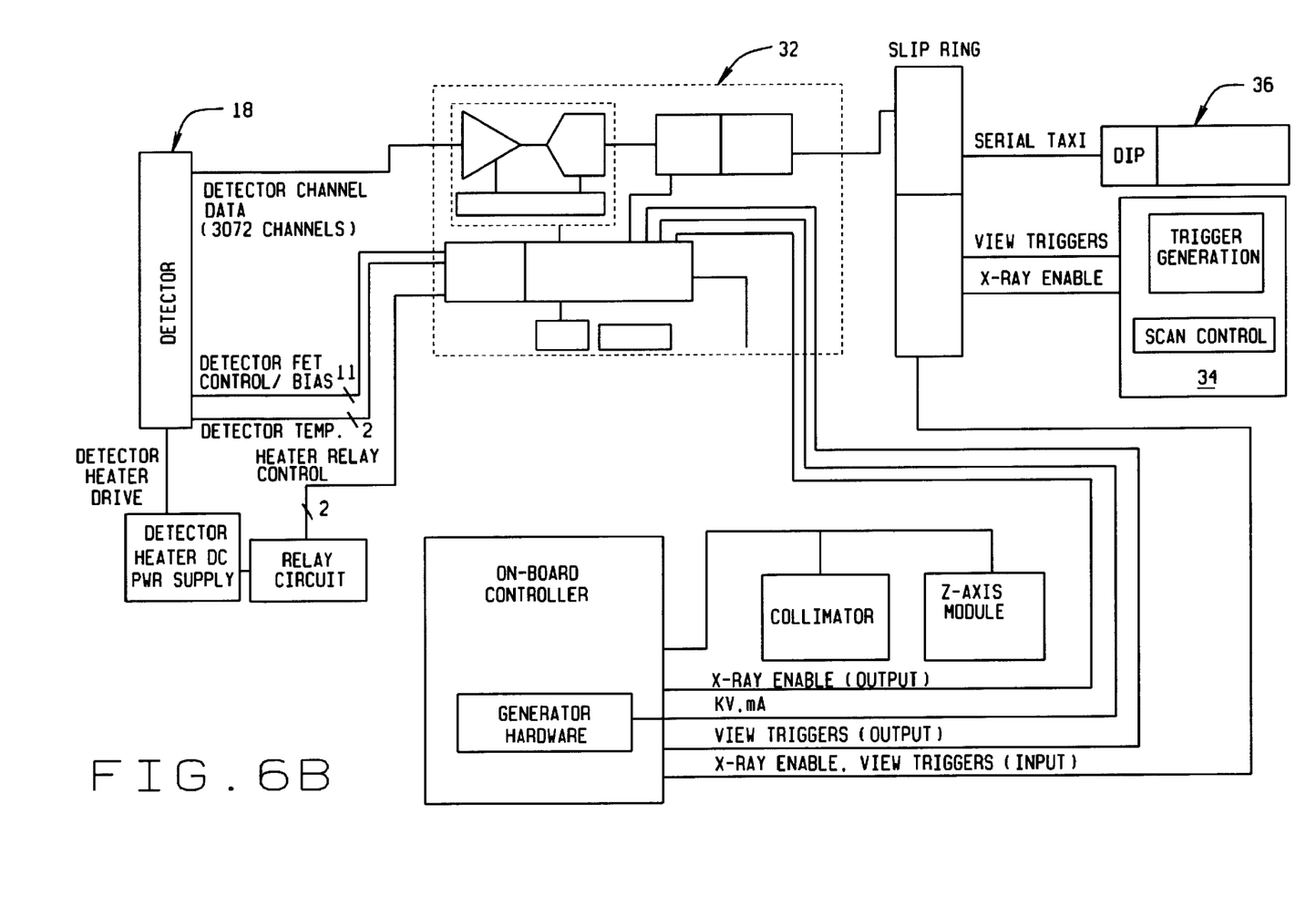

FIG. 6 is a functional block diagram of SDAS 32. As explained above, SDAS 32 processes low level analog signals from detector 18 into digital data. Once in digital form, the signal is manipulated and transmitted to computer 36 for storage. Several signal adjustments can be made via control registers contained on each converter board 104. For diagnostic purposes, SDAS 32 is configured to enable and set a special analog test voltage into the signal conditioning stage of the converter boards. In one embodiment, the test voltage will be programmable in 16384 steps between 0 and −3 volts. It is used in the diagnosis of the S-DAS acquisition and signal processing chain. The analog test signal can be enabled to either the input of the pre-amplifiers, or to a special test input channel. The firmware is further configured to set a I to 16 multiplication factor with respect to the test voltage when it is enabled into the pre-amplifier stage. The Analog to Digital (A/D) Converter block converts each supplied analog voltage to a digital word linearly proportional to the input signal level. In one embodiment, the outputs are read once per view and sent to computer 36.

In operation of system 10, the performance of certain components becomes reduced or de-graded so that it is necessary to identify and replace these components. For example, over time, the gain of certain cells of detector array 18 may become reduced, requiring identification and replacement of a detector array 18, or more specifically, detector module 58. Similarly, a channel or board 104 of DAS 32 may fail, requiring replacement of, for example, board 104. In addition, an interconnection between detector 18 and DAS 32 may fail, requiring replacement. In one embodiment, the configuration of system 10 is altered to fault isolate degraded components. More specifically, by altering the configuration of detector array 18 and DAS 32, a specific component of array 18, DAS 32, and the detector to DAS interconnection is identified as degraded so that component may be replaced, for example by a service technician.

Figure 7:
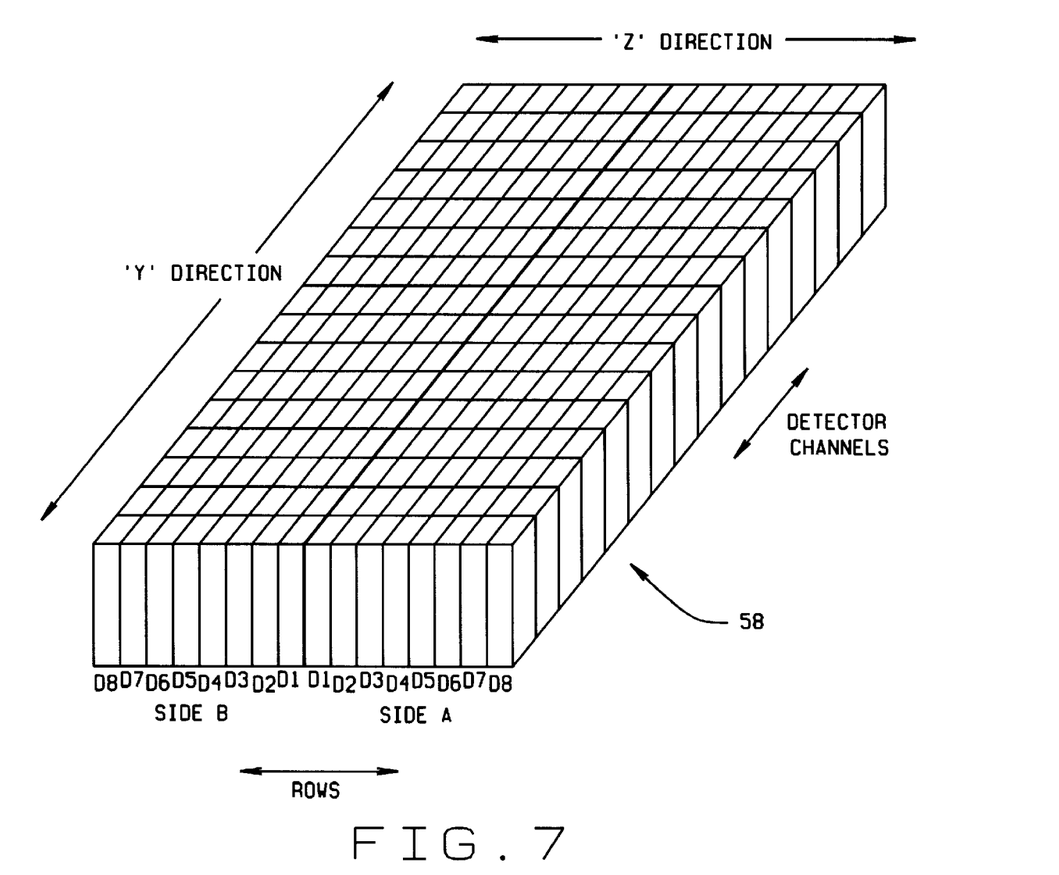
FIG. 7 is a perspective view of one embodiment of a detector module shown in FIG. 4.

More specifically and referring to FIG. 7, by utilizing row selection of detector array 18 and a series, or plurality of DAS channels and interconnections, specific tests, or patterns may be generated to fault isolate array 18, DAS 32, and the detector to DAS interconnection. Particularly, prior to performing a scan, the configuration of detector array 18 and DAS 32 are determined. For example, as described above, detector array 18 is configured in a system diagnostic mode with each slice being 1.25 mm and DAS 32 is configured to use a selected, or defined board 104 to convert the detector intensity data or signals. A scan is then performed so that detector intensity data is generated by detector array 18. Depending on the configuration of detector array 18, more specifically, decoder 68 and the FETs of switch apparatus 66, detector intensity data is generated for at least one row of detector cells. The detector intensity data is then electrically connected to DAS 32 using selected detector/DAS interconnections, for example cable 70. DAS 32 then generates digital data from the detector intensity data. More specifically, the detector intensity data is electrically connected to at least one defined, or selected board 104. The detector intensity data is then converted to digital data by board 104 of DAS 32.

Utilizing reference digital data from a reference scan having a defined detector array 18 configuration, x-ray source 14 voltage and current, and scan mode, the collected digital data may be compared to the reference digital data. Degraded component performance is determined by comparing the digital data from the scan to the reference digital data. More specifically, if the collected digital data does not favorably compare to, i.e., is equal to or within a defined tolerance of, the reference digital data, a degraded component is identified by fault isolation. In one embodiment, the reference scan may be a scan just completed, or a previously completed scan. A degraded component may be identified by performing a series of scans and by altering the configuration of detector array 18 and DAS 32 between each scan.

The degraded component is fault isolated by altering the configuration of detector array 18, DAS 32 and the interconnections. Specifically, different combination of detector cells are combined, the data is supplied to DAS 32 by different combinations of interconnections, and the detector intensity data is converted by different DAS boards 104. More specifically, unique intensity data patterns and combinations of detector cells are generated by detector array 18 by altering the configuration. Particularly, and as shown in Table 1, by enabling different combinations of FETs of switching apparatus 66, the detector intensity data is altered.

TABLE 1

| FET 4 | FET 3 | FET 2 | FET 1 | Mode | Row 2A | Row 1A | Row 1B | Row 2B |
|---|---|---|---|---|---|---|---|---|
| Gnd | Gnd | Gnd | Gnd | 4 × 1.25 mm | D2 | D1 | D1 | D2 |
| Gnd | Gnd | Gnd | −5.0 | 4 × 2.5 mm | D3 + D4 | D1 + D2 | D1 + D2 | D3 + D4 |
| Gnd | Gnd | −5.0 | Gnd | 4 × 3.75 mm | D4 + D5 + D6 | D1 + D2 + D3 | D1 + D2 + D3 | D4 + D5 + D6 |
| Gnd | Gnd | −5.0 | −5.0 | 4 × 5.0 mm | D5 + D6 + D7 + D8 | D1 + D2 + D3 + D4 | D1 + D2 + D3 + D4 | D5 + D6 + D7 + D8 |
| Gnd | −5.0 | Gnd | Gnd | Cal 1 | D3 | D2 | D2 | D3 |
| Gnd | −5.0 | Gnd | −5.0 | Cal 2 | D4 | D3 | D3 | D4 |
| Gnd | −5.0 | −5.0 | Gnd | Cal 3 | D5 | D4 | D4 | D5 |
| −5.0 | −5.0 | −5.0 | −5.0 | Cal 4 | D6 | D5 | D5 | D6 |
| −5.0 | Gnd | Gnd | Gnd | Cal 5 | D7 | D6 | D6 | D7 |
| −5.0 | Gnd | Gnd | −5.0 | Cal 6 | D8 | D7 | D7 | D8 |
| −5.0 | Gnd | −5.0 | Gnd | Cal 7 | D1 | D8 | D8 | D1 |
| Gnd | Gnd | −5.0 | −5.0 | Cal 8 | float | float | float | float |

Particularly, by enabling at least one FETs, at least one detector cell is identified to generate intensity data to be converted by DAS. A second pattern of detector data may be generated by enabling a different group of FETs so that a different detector cell or more than one detector cell is identified and outputs of the identified detector cells are combined to generate the detector data.

The detector data for the identified detector cells is then converted by DAS. DAS 32 is configured so that a selected channel of at least one board 104 is used to convert the detector intensity data to digital data. If the digital data is not equal to or within the specified tolerance range, in addition to altering the configuration of detector array 18, the configuration of DAS may be altered to generate fault isolation information. Specifically, the detector intensity data from detector array 18 may be converted using one, or more than one channel of a board 104, or by more than one board 104. By comparing the digital data from the performed scan, or first digital data, to the reference digital data, or second digital data, DAS 32 may be fault isolated. More specifically, by examining the digital data from the selected boards, a specific portion of board 104 or DAS 32 may be determined to be degraded. For example, if the detector intensity data is electrically connected to a group of four selected boards 104 and three of the selected boards 104 generate the proper digital data and the fourth selected board 104 generates incorrect digital data, the fault can be isolated to the fourth selected board 104 and the electrical connections from detector array 18 to the fourth selected board 104. To fault isolate between the electrical connections and the fourth board 104, DAS 32 may be configured to electrically connect the same detector intensity data to a group of selected channel of the fourth selected board 104. The group of selected channels may have one or more channels, for example, four channels, including a first channel, a second channel, a third channel and a fourth channel. If the first, second and third channels generate, or convert, the detector intensity data to the correct, or proper digital data, i.e., equal to the reference data, and the fourth selected channel does not, the fourth selected channel is fault isolated. If all four of the selected channels generate digital data which does not equal the reference data, the fault is in the electrical connection or the entire fourth selected board 104. By altering the configuration of detector array 18 and DAS 32 a series, or matrix of tests are executed to complete the fault isolation. In one embodiment, where all components are properly operating, the group of faulty components is empty, or contains zero components.

The matrix of defined tests along with the configuration of detector array 18 and DAS 32 may be stored as a fault isolation algorithm and stored in a memory of computer 36. Execution of the algorithm implements the tests described above and determines if the obtained results are equal to the expected or reference results. Use of the algorithm generates fault isolation information with little or no intervention by a service technician. In addition, the algorithm could be implemented as an expert system based on the configuration, test matrix, and fault isolation information.

The above described system utilizes the multislice detector array and the DAS boards to isolate faults so that specific degraded components are identified. In addition, the described system reduces the time required to isolate a failure and produces repeatable results without increasing the cost and complexity of the system.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used. Similarly, the systems described may be used with any multislice system. In addition, the fault isolation algorithm may be stored in computer 36 or in a separate host computer. Accordingly, the spirit and scope of the invention are to be limited only by the terms of the appended claims.

What is claimed is:

1. A method of troubleshooting an imaging system, the imaging system including an x-ray source for emitting an x-ray beam, a multislice detector, and a data acquisition system having a plurality of channels, said method comprising the steps of:
    altering a configuration of interconnections between the detector and the data acquisition system;
    performing a scan after said altering step;
    generating detector intensity data;
    generating digital data based on the detector intensity data;
    comparing the digital data to reference data having a defined detector configuration; and
    identifying a faulty component based on the comparison, and wherein altering a configuration of interconnections between the detector and the data acquisition system includes electrically connecting the same intensity data to a plurality of channels.

2. A method in accordance with claim 1 wherein the imaging system comprises a computer, and the altering, comparing, and identifying steps are performed automatically under control of the computer.

3. A method in accordance with claim 2 wherein the multislice detector comprises a plurality of detector modules, the identified faulty component is a detector module, and further comprising the step of replacing the faulty detector module.

4. A method in accordance with claim 2 wherein the data acquisition system comprises a plurality of boards, the identified faulty component is a detector acquisition system board, and further comprising the step of replacing the faulty detector acquisition system board.

5. A method in accordance with claim 2 wherein the identified faulty component is an interconnection between the detector and the data acquisition system, and further comprising the step of replacing the faulty interconnection.

6. A method in accordance with claim 1 wherein the detector array further comprises a plurality of field effect transistors, and wherein altering a configuration of interconnections between the detector and the data acquisition system comprises the step of enabling different groups of field effect transistors.

7. A method in accordance with claim 1 wherein altering a configuration of interconnections between the detector and the data acquisition system comprises the step of combining groups of detector cells to generate additional detector data.

8. A method in accordance with claim 1 wherein converting the detector intensity data to digital data comprises the steps of:
    converting the detector intensity data to first digital data using a first channel of the plurality of channels; and
    converting the detector intensity data to second digital data using a second channel of the plurality of channels.

9. A method in accordance with claim 8 wherein identifying a faulty component further comprises the step of comparing the first digital data to the second digital data.

10. An imaging system configured for troubleshooting, said imaging system comprising:
    a multislice detector array;
    a data acquisition system including a plurality of channels; and
    an x-ray source configured to emit an x-ray beam toward the multislice detector array, said data acguisition system configured to acquire and process data from said multislice detector array; said imaging system configured to:
        alter a configuration of interconnections between said detector array and said data acquisition system channels by electrically connecting the same intensity data to a plurality of channels;
        perform an x-ray scan after altering the configuration of interconnections;
        generate detector intensity data based on the scan;
        generate digital data based on the detector intensity data;

compare the digital data to reference data having a defined detector configuration; and identify a faulty component within said imaging system based on the comparison.

11. A troubleshooting system in accordance with claim 10 wherein the imaging system comprises a computer, and said troubleshooting system is configured to alter the configuration of interconnections between the data acquisition system prior to performing the scan, compare the original data to reference data having a defined detector configuration, and identify a fault component based on the comparison automatically under control of the computer.

12. A troubleshooting system in accordance with claim 11 wherein the multislice detector comprises a plurality of detector modules and said troubleshooting system is configured to identify fault detector modules.

13. A troubleshooting system in accordance with claim 11 wherein the data acquisition system comprises a plurality of boards and said troubleshooting system is configured to identify faulty detector acquisition system boards.

14. A troubleshooting system in accordance with claim 11 further comprising a plurality of interconnections between the detector and the data acquisition system, and said troubleshooting system is configured to identify faulty interconnections between the detector and the data acquisition system.

15. A troubleshooting system in accordance with claim 10 wherein to convert the detector intensity data to digital data, said troubleshooting system is configured to:

convert the detector intensity data to first digital data using a first channel of said plurality of channels; and convert the detector intensity data to second digital data using a second channel of said plurality of channels.

16. A troubleshooting system in accordance with claim 15 wherein to identify a faulty component, said troubleshooting system is further configured to compare the first digital data to the second digital data.

17. A troubleshooting system in accordance with claim 12 wherein the detector array further comprises a plurality of field effect transistors, and wherein to alter a configuration of interconnections between the detector and the data acquisition system, said troubleshooting system is configured to enable different groups of field effect transistors.

18. A troubleshooting system in accordance with claim 10 wherein to alter the configuration of interconnections between the detector and the data acquisition system, said troubleshooting system is configured to combine groups of detector cells to generate additional detector data.

* * * * *

UNITED STATES PATENT AND TRADEMARK OFFICE
CERTIFICATE OF CORRECTION

PATENT NO. : 6,246,743 B1
DATED : June 12, 2001
INVENTOR(S) : Rudolph T. Kopp, III et al.

Page 1 of 1

It is certified that error appears in the above-identified patent and that said Letters Patent is hereby corrected as shown below:

<u>Column 10,</u>
Line 13, delete "12" and substitute -- 10 --.

Signed and Sealed this

Sixteenth Day of April, 2002

Attest:

JAMES E. ROGAN
*Director of the United States Patent and Trademark Office*

*Attesting Officer*